United States Patent [19]

Sikkenga et al.

[11] Patent Number: 4,777,310

[45] Date of Patent: Oct. 11, 1988

[54] CATALYZED OLEFIN EQULIBRATION AND SEPARATION OF THE EQUILIBRATED PRODUCTS

[75] Inventors: David L. Sikkenga; Chander Balakrishnan, both of Wheaton, Ill.

[73] Assignee: Amoco Corporation, Chicago, Ill.

[21] Appl. No.: 139,329

[22] Filed: Dec. 30, 1987

Related U.S. Application Data

[63] Continuation of Ser. No. 20,788, Mar. 2, 1987, abandoned, which is a continuation of Ser. No. 870,823, Jun. 5, 1986, abandoned.

[51] Int. Cl.$^4$ .............................................. C07C 6/02
[52] U.S. Cl. ..................... 585/415; 585/525; 585/643; 585/649; 585/671
[58] Field of Search ............... 585/415, 525, 643, 648, 585/649, 644, 671

[56] References Cited

U.S. PATENT DOCUMENTS

| | | | |
|---|---|---|---|
| 4,409,421 | 10/1983 | Herwig et al. | 585/833 |
| 4,451,685 | 5/1984 | Nevitt et al. | 585/415 |
| 4,499,325 | 2/1985 | Klotz et al. | 585/671 |
| 4,499,326 | 2/1985 | Melquist | 585/671 |
| 4,503,282 | 3/1985 | Sikkenga | 585/671 |

*Primary Examiner*—Asok Pal
*Attorney, Agent, or Firm*—Reed F. Riley; William H. Magidson; Ralph C. Medhurst

[57] ABSTRACT

A method for the selective gas-phase equilibration of at least one $C_3$ or greater monoalkene over a HAMS-1B crystalline borosilicate-based catalyst composition employing operating conditions in which the total butylene and t-amylene $C_5$ and lower fraction of the product are maximized and the formation of $C_1$ to $C_3$ hydrocarbons, total aromatics and total paraffins are minimized. In another aspect of the invention the equilibration product is usefully separated by converting the isobutylene and t-amylene fractions to their methyl ethers by reaction with methanol.

9 Claims, No Drawings

CATALYZED OLEFIN EQUILIBRATION AND SEPARATION OF THE EQUILIBRATED PRODUCTS

This is a continuation of application Ser. No. 020,788 filed Mar. 2, 1987 which is a continuation of application Ser. No. 870,823 filed June 5, 1986 abandoned.

BACKGROUND OF THE INVENTION

This invention relates to a process for selectively equilibrating a $C_3$ or greater monoalkene to a hydrocarbon mixture using a HAMS-1B crystalline borosilicate-based catalyst composition in which the production of total butylenes and t-amylenes is substantially enhanced. More particularly, this invention relates to the selective gas-phase equilibration of at least one $C_3$ or greater monoalkene over a HAMS-1B crystalline borosilicate-based catalyst composition to a largely olefin mixture employing operating conditions which maximize the n-butenes and isobutylene portion of the $C_4$ fraction and the t-amylene portion of the $C_5$ fraction and minimize the formation of $C_1$ to $C_3$ hydrocarbons, total aromatics, and total paraffins; such mixture is usefully separated in one aspect of the invention by reaction with methanol to form the methyl ethers of isobutylene and the t-amylenes.

The commercial preparation of olefins involves thermally cracking a hydrocarbon feedstock such as gas oil, naphtha, or an ethane-propane combination. With each of these feedstocks propylene is a major product and accompanies other olefins and diolefins, such as ethylene and butadiene, and additional hydrocarbons. The particular distribution of products for a given feedstock is relatively fixed which can lead to overproduction of one olefin product to meet the demand for another product or products from the cracking process. Thus, it is desirable to develop "add-on" processes which can be utilized in conjunction with the thermal cracking process to convert a product produced in market excess to other products in shorter supply and of more commercial value. Unlike the thermal cracking process, such "add-on" processes need to be catalytic since they should be selective in converting the excess product.

In particular, it is of advantage to be able to economically convert propylene when it is in long supply to higher value products useful in the transportation fuel industry since the transportation fuel market is enormous and can absorb large quantities of suitably converted excess "cracker" propylene. If propylene could be converted economically to a process stream rich in total butylenes and t-amylenes, diversion of the excess propylene to the gasoline market is possible since new regulations covering the amount of lead in gasoline have forced refiners to seek new sources of octane, one of which is the methyl ethers of isobutylene and t-amylenes, MTBE and TAME, respectively. The methanol required to make these ethers is inexpensive and plentiful and the isobutylene and t-amylenes are generally the limiting components. In addition, linear butenes are the preferred feedstock for the acid catalyzed alkylation of isobutane to make high octane fuel supplements. Thus, a process to convert propylene selectively to total butylenes and t-amylenes could have substantial economic value.

Now, catalyzed equilibration processes have been found to selectively convert propylene and higher olefins to largely olefin products containing a high proportion of total butylenes and t-amylenes while reducing the formation of total paraffins and $C_1$–$C_3$ hydrocarbons. These processes when combined with existing technology for conversion of isobutylene and t-amylenes to their methyl ethers and n-butenes to "alkylate" can economically convert propylene and other olefins to valuable products having an essentially unlimited market.

A number of processes for catalytically processing olefins have been taught in the past; for example, in U.S. Pat. No. 4,451,685 a process is described to convert propylene to gasoline blending stock which comprises contacting an AMS-1B crystalline borosilicate-based catalyst with $C_2$–$C_3$ olefins. The $C_2$–$C_3$ olefins are converted to a mixture of alkanes, alkenes, branched alkanes and alkenes, and aromatics useful as a gasoline blending stock. Olefin interconversion product distributions resulting from propylene conversions over HZSM aluminosilicate zeolites as a function of space velocity and temperature are described at p. 109 in "Catalysis by Intermediate Pore Zeolites," an article in the Proceedings of the Second Symposium of the Industry—University Cooperative Chemistry Program of the Department of Chemistry, Texas A&M University, Apr. 1–4, 1984. In U.S. Pat. No. 4,503,282, a process to convert a substantially linear alkene, such as n-butene, to isomerized products is taught, which process comprises contacting such alkene at a temperature above about 300° to about 650° C. and an alkene reactant partial pressure of less than about 0.4 atmospheres with an AMS-1B borosilicate-supported catalyst containing at least 50 weight percent hydrogen form AMS-1B. As the described process is an isomerization, essentially all the products have the same carbon number as the starting alkene. A method to convert an alkene to oligomerized, aromatized, or isomerized products over an AMS-1B borosilicate-based catalyst system is taught in U.S. Pat. No. 4,499,325. Methods are taught by which linear butenes, for example, can be converted to isobutylene, dimerized to $C_8$ products and converted to aromatics. Converting organic compounds over a catalyst comprising a zeolite of altered activity resulting from reacting the zeolite either "as synthesized" or initially ion exchanged, with a compound having a complex fluoroanion which could include a fluoroborate is taught in U.S. Pat. No. 4,500,421. In U.S. Pat. No. 4,456,779, processes of converting pressurized liquid olefins to a mixture containing a high proportion of $C_{5+}$ hydrocarbons in the gasoline boiling and distillate range are taught. Such processes are carried out over an acid ZSM-5 type catalyst. The processing of light olefins (2 to 4 carbon atoms) to products comprising either high octane olefin gasoline components or high octane aromatic gasoline components is taught in U.S. Pat. No. 4,150,062. U.S. Pat. No. 4,456,582 teaches the preparation and use of molecular sieves including a borosilicate for catalytic purposes including propylene oligomerization to mixtures containing aromatics, aliphatics, and, primarily, $C_5$ to $C_9$ olefins. In U.S. Pat. Nos. 2,242,530, 4,307,254, and 4,336,407, a method of reacting and separating isoolefins from hydrocarbon mixtures using combined reaction (with methanol) and distillation is taught. $C_4$ and $C_5$ isoolefins are among those taught as useful in this catalytic distillation process.

SUMMARY OF THE INVENTION

Described herein is a process for equilibrating at least one $C_3$ or greater monoalkene to a low total paraffins, high total butylenes, and high t-amylenes containing product which comprises contacting such alkene with a HAMS-1B crystalline borosilicate-based catalyst composition at a catalyst contact time of between about 0.1 and about 3.0 seconds in the temperature range from about 280° to about 550° C. while maintaining the partial pressure of said alkene at a value calculated by the function AT/1000 where A is a number varying between about 7 psia/°C. and about 180 psia/°C., and T is the temperature in °C. The equilibration product in another aspect of the invention is usefully separated by reaction of essentially all the isobutylene and t-amylene portions with methanol to form their methyl ethers.

DETAILED DESCRIPTION OF THE INVENTION

The catalyzed equilibration process of the instant invention equilibrates at least one $C_3$ or greater monoolefin; e.g., propylene, a n-butene, isobutylene, a n-pentene or a branched $C_5$ olefin, a n-hexene or a branched hexene, etc. More preferably, at least one $C_3$ to $C_{12}$ monoolefin, linear or branched, is used. Propylene or at least one $C_4$ alkene is the preferred olefin feed to be equilibrated. Mixtures of monoolefins can be used as well; for example, after the total butylenes and t-amylenes have been separated from the equilibration product exiting the HAMS-1B reactor, the olefins remaining in the product can be recycled to the equilibration reactor to produce additional total butylenes and t-amylenes. By total butylenes is meant isobutylene and 1- and 2-butene. By t-amylenes is meant 2-methyl-1-butene and 2-methyl-2-butene.

Additional hydrocarbons may accompany the feed olefin or olefins. For example, a propane/propylene or a butane/butene mixture can be used. Additionally, inert gaseous diluents such as steam, nitrogen, saturated hydrocarbons and the like may be employed.

The product from the catalyzed equilibration process desirably contains less than about 10 weight percent total paraffins, more preferably less than about 8 weight percent total paraffins. In addition, the product desirably contains greater than about 12 weight percent total butylenes and about 10 weight pecent t-amylenes, more preferably greater than about 14 weight percent total butylenes and about 12 weight percent t-amylenes.

The process is carried out above about 280° C., a temperature which is high enough for the proper equilibration reactions to take place over the HAMS-1B catalyst composition. The preferred temperature range is from about 280° to 550° C.

Catalyst composition contact times should be relatively short or higher molecular weight and/or aliphatic and aromatic products are formed at the expense of the desired $C_4$ and $C_5$ monoolefins. Contact times should be in the range of about 0.1 to about 3.0 seconds and more preferably be in the range from about 0.3 to about 2.5 seconds.

The desired partial pressure of the monoolefin feed is a function of temperature and its temperature dependence can be represented as follows:

$$\text{olefin partial press.} = \frac{AT}{1000}$$

where A is a constant varying between 7 and about 180, and T is the temperature in °C. Thus, preferred olefin partial pressures run between about 1.4 and about 99 psia, more preferably between about 2.5 and about 82.5 psia.

Although a fixed bed reactor is preferred to carry out the process of the instant invention, the equilibration process can be operated in a fluidized bed mode or in another type of reactor design. Changes in the physical characteristics of the catalyst compositions used may be required if reactor mode is changed as can be understood by one skilled in the art.

Separation of the total butylenes and t-amylenes from the product can be accomplished by conventional fractionation. The remaining hydrocarbons, largely $C_6$ to $C_{10}$ olefins and $C_1$–$C_3$ light ends, can be recycled to the equilibration reactor and equilibrated to additional total butylenes and t-amylenes.

In another aspect of the invention, the isobutylene and t-amylenes portion of the equilibration mixture can be separated from the equilibration mixture by converting them to their methyl ethers for use, for example, in transportation fuels. The product stream from the HAMS-1B equilibration reactor, generally after compression, can be fed to a catalytic distillation unit or other reactor-separator combination where process conditions are such that essentially only the isobutylene and t-amylenes in the $C_4$–$C_5$ fraction react in the presence of a catalyst with methanol to form their methyl ethers. The light ends and linear $C_4$ olefins are taken overhead and the linear $C_4$ olefins can be separated and used for "alkylate" production or recycled to the equilibration reactor to be equilibrated. The MTBE and TAME formed by methanol addition to isobutylene and the t-amylenes can be removed from the bottom of the unit and, after separation of these ethers, the remaining $C_{5+}$ fraction can be used for gasoline blending or recycled to the equilibration reactor. This technique combines in an economic way the separation of the $C_4$ and $C_5$ fraction and conversion of the isobutylene and t-amylenes to their methyl ethers. Process condition and catalysts for catalytic distillation and other reactor-separator combinations are well known to those skilled in the art.

The catalyst compositions used in this invention are based on the AMS-1B crystalline borosilicate molecular sieve which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

$$0.9 \pm 0.2 M_{2/n}O{:}B_2O_3{:}ySiO_2{:}zH_2O$$

wherein M is at least one cation, n is the valence of the cation, y is between 4 and about 600, and z is between 0 and about 160.

TABLE A

| d-Spacing Å[1] | Assigned Strength[2] |
|---|---|
| [1]11.2 ± 0.2 | W–VS |
| [1]10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

[1]Copper K alpha radiation
[2]VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and m is at least one cation having a valence n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates, and Ludox, a stabilized polymer of silicic acid manufactured by E. I. du Pont de Nemours & Company. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate-molecular sieve can be prepared by crystallizing a mixture of sources for an oxide of silicon, an oxide of boron, an alkylammonium compound, and ethylenediamine such that the initial reactant molar ratios of water to silica range from about 5 to about 25, preferably about 5 to about 20, and most preferably from about 10 to about 15. In addition, preferable molar ratios for the initial reactant of silica to an oxide of boron range from about 4 to about 150, more preferably from about 5 to about 80, and most preferably from about 5 to about 20. The molar ratio of ethylenediamine to silicon oxide should be about above about 0.05, typically below 5, preferably between about 0.1 and about 1.0, and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1, and most preferably about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days, and preferably is about one to about seven days, at a temperature ranging from about 100° to about 250° C., preferably from about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and to determine the optimum crystallization time.

The crystalline material formed can be separated and recovered by well-known means such as filtration with aqueous washing. This material can be mildly dried for anywhere from a few hours to a few days at varying temperatures, typically about 50° to 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB, and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc, and cadmium. Specific combinations of nonnoble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well known in the art. Typically, an aqueous solution of a cationic species is exchanged one or more times at about 25° to about 100° C. A hydrocarbon-soluble metal compound, such as a metal carbonyl, also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays, such as bentonite or kaolin, or other binders well known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 weight percent of the total composition. Catalytic compositions can contain about 0.1 weight percent to about 100 weight percent crystalline borosilicate material, preferably contain about 10 weight percent to about 95 weight percent of such material, and most preferably contain about 20 weight percent to about 80 weight percent of such material.

Catalytic compositions comprising the crystalline borosilicate material of this invention and a suitable matrix material can be formed by adding a finely divided crystalline borosilicate and a catalytically active metal compound to an aqueous sol or gel of the matrix material. The resulting mixture is thoroughly blended and gelled, typically by adding a material such as ammonium hydroxide. The resulting gel can be dried and calcined to form a composition in which the crystalline borosilicate and catalytically active metal compound are distributed throughout the matrix material.

The following Examples will serve to illustrate certain embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

Unless otherwise noted, all conversions were accomplished using a 0.18-inch diameter reactor heated in a sand bath and packed with 4.0 g of a HAMS-1B catalyst composition made according to the teachings of U.S. Pat. No. 4,268,420. The reactor effluent, gas and liquid, was separated to yield a gaseous product analyzed using a column containing 5 feet of DC-11 on chromosorb and 15 feet of picric acid on Graphpac-GC. The liquid product was analyzed on a 50-meter capillary column with a crosslinked methyl silicone coating. Product compositions are given in weight percents of the particular component.

EXAMPLES 1-3

In these Examples, propylene was converted over a catalyst composition containing 40 weight percent HAMS-1B sieve matrixed with 60 weight percent of $\gamma$-$Al_2O_3$. The data are given in Table I below.

TABLE I

| Conditions | Examples | | |
|---|---|---|---|
| | 1 | 2 | 3 |
| Propylene WHSV (g feed/hr/g cat) | 5.9 | 5.9 | 5.9 |
| Diluent | $H_2O$ | $H_2O$ | $H_2O$ |
| Diluent/Propylene (mol ratio) | 3.2 | 3.2 | 3.2 |
| Pressure (psig) | 7 | 6 | 5 |
| Temp. (°C.) | 371 | 332 | 290 |
| Propylene Partial Pressure (psia) | 5 | 5 | 5 |
| Contact Time (sec) | 0.44 | 0.45 | 0.46 |
| Product Composition wt. % | | | |
| Methane | 0.005 | 0.002 | 0 |
| Ethane | 0.008 | 0.004 | 0.002 |
| Ethylene | 1.45 | 0.57 | 0.074 |
| Propane | 2.11 | 1.64 | 1.79 |
| Propylene | 15.7 | 13.4 | 12.6 |
| Butanes | 5.32 | 3.27 | 0.82 |
| Isobutylene | 12.0 | 12.9 | 8.75 |
| n-Butenes | 11.5 | 11.2 | 11.1 |
| t-Amylenes | 11.4 | 15.1 | 16.1 |
| other $C_5$'s | 6.2 | 6.6 | 5.74 |
| $C_6$+ | 34.2 | 35.3 | 43.1 |
| Total Butylenes plus t-Amylenes | 34.9 | 39.2 | 36.0 |

EXAMPLES 4-6

In these Examples, propylene was converted over a catalyst composition containing 40 weight percent HAMS-1B sieve matrixed with 60 weight percent of kaolin. The data are given in Table II below.

TABLE II

| Conditions | Examples | | |
|---|---|---|---|
| | 4 | 5 | 6 |
| Propylene WHSV (g feed/hr/g cat) | 5.9 | 5.9 | 5.9 |
| Diluent | None | None | None |
| Diluent/Propylene (mol ratio) | 0 | 0 | 0 |
| Pressure (psig) | 2 | 2 | 2 |
| Temp. (°C.) | 436 | 317 | 357 |
| Propylene Partial Pressure (psia) | 17 | 17 | 17 |
| Contact Time (sec) | 0.81 | 0.97 | 0.92 |
| Product Composition wt. % | | | |
| Methane | 0.02 | 0.001 | 0.002 |
| Ethane | 0.02 | 0.01 | 0.04 |
| Ethylene | 1.57 | 0.11 | 0.37 |
| Propane | 2.17 | 1.92 | 2.06 |
| Propylene | 20.8 | 5.19 | 7.41 |
| Butanes | 1.55 | 0.67 | 2.07 |
| Isobutylene | 13.5 | 6.15 | 10.9 |
| n-Butenes | 16.1 | 8.08 | 10.4 |
| t-Amylenes | 13.4 | 17.0 | 17.5 |
| other $C_5$'s | 3.78 | 6.17 | 7.17 |
| $C_6$+ | 27.1 | 54.7 | 42.1 |
| Total Butylenes plus t-Amylenes | 43 | 31.2 | 38.8 |

EXAMPLES 7-9

In these Examples, propylene was converted over a catalyst composition containing 40 weight percent HAMS-1B sieve matrixed with 60 weight percent $\gamma$-$Al_2O_3$. The data are given in Table III below.

TABLE III

| Conditions | Examples | | |
|---|---|---|---|
| | 7 | 8 | 9 |
| Propylene WHSV (g feed/hr/g cat) | 12 | 6 | 2.8 |
| Diluent | None | None | Helium |
| Diluent/Propylene (mol ratio) | 0 | 0 | 1 |
| Pressure (psig) | 15 | 2 | 2 |
| Temp. (°C.) | 356 | 358 | 358 |
| Propylene Partial Pressure (psia) | 30 | 17 | 8.5 |
| Contact Time (sec) | 0.81 | 0.90 | 0.99 |
| Product Composition wt. % | | | |
| Methane | 0.001 | 0.001 | 0 |
| Ethane | 0.02 | 0.02 | 0.02 |
| Ethylene | 0.21 | 0.25 | 0.25 |
| Propane | 1.96 | 2.02 | 0.87 |
| Propylene | 5.70 | 9.03 | 17.4 |
| Butanes | 1.13 | 1.11 | 0.78 |
| Isobutylene | 9.15 | 11.1 | 12.2 |
| n-Butenes | 9.19 | 10.5 | 15.4 |
| t-Amylenes | 17.4 | 17.2 | 11.6 |
| other $C_5$'s | 7.84 | 7.6 | 6.18 |
| $C_6$+ | 47.5 | 41.2 | 35.3 |
| Total Butylenes plus t-Amylenes | 35.7 | 38.8 | 39.2 |

COMPARATIVE EXAMPLES 10 AND 11

These Examples converted propylene over a catalyst composition containing 40 weight percent HAMS-1B sieve and 60 weight percent $\gamma$-$Al_2O_3$. They show the effect on product composition of changing process variables to values outside those producing the desired product slate. The data are given in Table IV below.

TABLE IV

| Conditions | Examples | |
|---|---|---|
| | 10 | 11 |
| Propylene WHSV (g feed/hr/g cat) | 1.7 | 5.9 |
| Diluent | $H_2O$ | None |
| Diluent/Propylene (mol ratio) | 5.2 | 0 |
| Pressure (psig) | 8 | 46 |
| Temp. (°C.) | 533 | 323 |
| Propylene Partial Pressure (psia) | 3.6 | 61 |
| Contact Time (sec) | 0.53 | 3.5 |
| Product Composition wt. % | | |
| Methane | 0.05 | — |
| Ethane | 0.07 | 0.04 |
| Ethylene | 3.27 | 0.08 |
| Propane | 0.97 | 0.79 |
| Propylene | 77.5 | 8.74 |
| Butanes | 0.05 | 0.46 |
| Isobutylene | 4.62 | 4.11 |
| n-Butenes | 6.87 | 8.09 |
| t-Amylenes | 1.8 | 9.5 |
| other $C_5$'s | 4.8 | 68.2 |
| Total Butylenes plus t-Amylenes | 13.3 | 21.7 |

EXAMPLES 12 AND 13

In these Examples a 1 cm i.d. reactor was employed and the amount of catalyst composition was 5.6 g. The feeds to the reactor were mixtures, the compositions of which together with the other data are given in Table V below. Conversion was accomplished using a catalyst composition containing 40 weight percent HAMS-1B sieve matrixed with 60 weight percent $\gamma$-$Al_2O_3$.

TABLE V

Olefin Interconversion With Different Feeds

| | Examples | | | |
|---|---|---|---|---|
| Conditions | 12 | | 13 | |
| Feed WHSV (g feed/hr/g cat) | 3.3 | | 2.8 | |
| Diluent | None | | Hydrogen | |
| Diluent/Olefin (mol ratio) | — | | 27 | |
| Pressure (psig) | 1 | | 27 | |
| Temp. (°C.) | 330 | | 396 | |
| Olefin Partial Pressure (psia) | 12 | | 4.1 | |
| Contact Time (sec) | 1.14 | | 1.6 | |

| Feed and Compositions (wt. %) | Feed | Product | Feed | Product |
|---|---|---|---|---|
| Methane | 0.074 | 0.07 | — | 0.02 |
| Ethane | 0.90 | 0.73 | — | 0.01 |
| Ethylene | 0.63 | 0.58 | — | 0.72 |
| Propane | 19.0 | 14.8 | — | 0.54 |
| Propylene | 78.6 | 9.51 | — | 16.0 |
| Butanes | 0.18 | 1.18 | 6.30 | 6.27 |
| Isobutylene | 0.10 | 9.57 | 0.07 | 12.8 |
| n-Butenes | 0.28 | 12.0 | 1.16 | 14.8 |
| t-Amylenes | — | 12.5 | 0.30 | 12.6 |
| other $C_5+$ | 0.25 | 39.1 | 92.2 | 36.2 |
| Total Butylenes plus t-Amylenes | — | 34.1 | — | 40.2 |

EXAMPLES 14–18

These Examples show the effect on product distributions of changing the feed olefin. The catalyst composition contained 40 weight percent HAMS-1B matrixed in 60 weight percent kaolin. A 1-cm i.d. reactor was employed. The data are given in Table VI below.

TABLE VI

| | Examples | | |
|---|---|---|---|
| Conditions | 14 | 15 | 16 |
| Hydrocarbon Feed | $C_3H_6$ | $i-C_4H_8$ | $i-C_5H_{10}$ |
| Feed Rate (g/hr) | 39 | 16.8 | 53.9 |
| Water Feed Rate (g/hr) | 14.6 | 6.3 | 14.0 |
| Catalyst Wt. (g) | 5.6 | 5.6 | 5.6 |
| Avg. Reactor Temp. (°C.) | 449 | 418 | 412 |
| Reactor Pressure (psig) | 1.6 | 0.9 | 1.0 |
| WHSV (g HC/hr/g cat) | 7.1 | 3.0 | 9.6 |
| Olefin Partial Pressure (psia) | 8.8 | 8.5 | 10.3 |
| Contact Time (sec) | 0.36 | 0.37 | 0.56 |
| Product Composition (wt. %) | | | |
| $CH_4$ | 0.01 | 0.02 | 0.01 |
| $C_2H_4$ | 2.09 | 2.53 | 1.48 |
| $C_2H_6$ | 0.0 | 0.2 | 0.08 |
| $C_3H_6$ | 29.6 | 17.8 | 12.3 |
| $C_3H_8$ | 1.55 | 1.59 | 0.91 |
| $Iso-C_4H_8$ | 14.8 | 15.0 | 12.9 |
| $n-C_4H_8$ | 19.9 | 17.8 | 15.3 |
| $C_4H_{10}$ | 1.25 | 1.22 | 3.96 |
| $C_5+$ | 30.8 | 38.2 | 53.1 |
| Total Butylenes | 34.7 | 32.8 | 28.1 |

| | Examples | |
|---|---|---|
| Conditions | 17 | 18 |
| Hydrocarbon Feed | $C_{12}$ α-olefin | $C_5+$ Recycled |
| Feed Rate (g/hr) | 53 | 26.3 |
| Water Feed Rate (g/hr) | 12.6 | 6.0 |
| Catalyst Wt. (g) | 5.6 | 5.6 |
| Avg. Reactor Temp. (°C.) | 411 | 404 |
| Reactor Pressure (psig) | 1.1 | 0.9 |
| WHSV (g HC/hr/g cat) | 9.4 | 4.6 |
| Olefin Partial Pressure (psia) | 4.9 | 7.8 |
| Contact Time (sec) | 0.65 | 0.98 |
| Product Composition (wt. %) | | |
| $CH_4$ | 0.01 | 0.01 |
| $C_2H_4$ | 1.48 | 1.66 |
| $C_2H_6$ | 0.09 | 0.10 |
| $C_3H_6$ | 12.7 | 12.1 |
| $C_3H_8$ | 0.92 | 1.01 |
| $Iso-C_4H_8$ | 12.8 | 11.9 |
| $n-C_4H_8$ | 15.2 | 13.7 |
| $C_4H_{10}$ | 3.71 | 3.83 |
| $C_5+$ | 53.1 | 55.8 |
| Total Butylenes | 28.0 | 25.6 |

EXAMPLE 19

A propylene stream (99.5% propylene and 0.5% propane) was run through a fixed bed equilibration reactor at a temperature of 358° C., 2 psig total pressure and a WHSV of 6 $hr^{-1}$. Olefin partial pressure was 16.7 psia and catalyst composition contact time was 0.9 seconds. The product from this reactor after compression was led into a catalytic distillation tower containing a supported acidic cationic ion exchange resin operated at 150 psia. The feed rate of the hydrocarbon stream to the catalytic distillation tower was about 200 g/min and the feed rate of methanol was about 25.4 g/min. The temperature of the overhead was about 110° F. and the bottoms about 320° F. The temperature of the reaction zone was about 200° F. The composition data is shown in the Table below.

TABLE VII[3]

| Component | OE[1] Feed Comp. | OE[1] Product Comp. | MeOH/ 100 g OE Feed | Cat. Dist. Ovhd. | Cat. Dist. Bttms. | Cat. Dist. Bttm. Comp. Normalized | Calculated R + M/2 Octane No. |
|---|---|---|---|---|---|---|---|
| $C_1 + C_2$ | | 0.27 | | 0.27 | | | |
| Propane | 0.5 | 2.02 | | 2.02 | | | |
| Propylene | 99.5 | 9.03 | | 9.03 | | | |
| Butanes | | 1.11 | | 1.11 | | | |
| Isobutylene | | 11.1 | 6.03[2] | 0.55 | | | |
| n-Butenes | | 10.5 | | 10.5 | | | |
| t-Amylenes | | 17.2 | 6.68[2] | 2.58 | | | |
| $n-C_5$ | | 7.6 | | 7.6 | | | |
| $C_6+$ | | 41.2 | | | 41.2 | 52.1 | 85 |
| MTBE[2] | | | | | 16.55 | 20.9 | 103 |
| TAME[2] | | | | | 21.3 | 26.9 | 99 |
| Totals | 100.0 | 100.0 | 12.71 | 33.66 | 79.05 | 100.0 | 92 |

[1]Olefin equilbration
[2]95% isobutylene conversion and 85% t-amylene conversion
[3]Compositions are per 100 g of OE feed

What is claimed is:

1. An equilibration process for converting a mixture comprising at least one $C_3$ or greater monoalkene to a low total paraffin, greater than about 31 weight percent total butylenes and t-amylenes containing product in which total aromatics are minimized, that comprises contacting such alkene with a catalyst composition comprising a HAMS-1B crystalline borosilicate molecular sieve incorporated into an organic matrix at a catalyst composition contact time of between about 0.1 and about 3.0 seconds in the temperature range from about 280° to about 550° C. while maintaining the partial pressure of said alkene at a value calculated by the function AT/1000 where A is a number varying between about 7 psia/°C. and about 180 psia/°C. and T is the temperature in °C.

2. The process of claim 1 wherein said monoalkene is at least one $C_3$ to $C_{12}$ alkene.

3. The process of claim 1 wherein said monoalkene is propylene or at least one $C_4$ alkene.

4. The process of claim 1 wherein said mixture comprises propane and propylene.

5. The process of claim 1 wherein said mixture comprises a product from a thermal cracking olefins unit.

6. A process comprising:
(a) equilibrating a feed stream comprising at least one $C_3$ to $C_{12}$ mnoalkene with a catalyst composition comprising a HAMS-1B crystalline borosilicate molecular sieve incorporated into an organic matrix at a catalyst contact time of between 0.1 and about 3.0 seconds in the temperature range from about 280° to about 550° C. while maintaining the partial pressure of said alkene at a value calculated by the function AT/1000 where A is a number varying between about 7 psia/°C. and about 180 psia/°C. and T is the temperature in °C. to form a product stream low in total paraffins, greater than about 31 weight percent in total butylenes and t-amylenes, and in which total aromatics are minimized;
(b) compressing and reacting said product stream with methanol such that essentially only the isobutylene and t-amylene portion of the $C_4$-$C_5$ fraction forms methyl ethers, to form a reaction product; and
(c) separating said reaction product into a higher boiling component comprising essentially all said methyl ethers and unreacted $C_5+$ components and a lower boiling component.

7. The process of claim 6 wherein said monoalkene is propylene or at least one $C_4$ alkene.

8. A process comprising:
(a) equilibrating a feed stream comprising at least one $C_3$ to $C_{12}$ monoalkene with a catalyst composition comprising a HAMS-1B crystalline borosilicate molecular sieve incorporated into an inorganic matrix at a catalyst contact time of between 0.1 and about 3.0 seconds in the temperature range from about 280° C. to about 550° C. while maintaining the partial pressure of said alkene at a value calculated by the function AT/1000 where A is a number varying between about 7 psia/°C. and about 180 psia/°C. and T is the temperature in °C. to form a product stream low in total paraffins, greater than about 31 weight percent in total butylenes and t-amylenes, and in which total aromatics are minimized;
(b) compressing and separating said product stream into a higher boiling $C_6+$ component which is recycled to said feed stream and a lower boiling component;
(c) reacting said lower boiling component with methanol such that essentially only the isobutylene and t-amylenes portion of said lower boiling component reacts to form methyl ethers, to form a reaction product; and
(d) separating said reaction product into a higher boiling component containing essentially all said ethers and a lower boiling component which is recycled to said feed stream.

9. The process of claim 8 wherein said monoalkene is propylene or at least one $C_4$ alkene.

* * * * *